(12) United States Patent
Squire et al.

(10) Patent No.: US 11,229,440 B2
(45) Date of Patent: Jan. 25, 2022

(54) SYSTEMS AND METHODS FOR VASCULAR OCCLUSION

(71) Applicant: BOSTON SCIENTIFIC SCIMED, INC., Maple Grove, MN (US)

(72) Inventors: Robert Squire, Maple Grove, MN (US); Joel Munsinger, Blaine, MN (US); Derek Larson, Golden Valley, MN (US); Martin Willard, Burnsville, MN (US); Joseph Connolly, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 126 days.

(21) Appl. No.: 15/083,245

(22) Filed: Mar. 28, 2016

(65) Prior Publication Data

US 2016/0310147 A1    Oct. 27, 2016

Related U.S. Application Data

(60) Provisional application No. 62/138,508, filed on Mar. 26, 2015.

(51) Int. Cl.
  *A61B 17/12* (2006.01)
  *A61B 17/42* (2006.01)
  (Continued)

(52) U.S. Cl.
  CPC .. *A61B 17/12172* (2013.01); *A61B 17/12022* (2013.01); *A61B 17/12109* (2013.01);
  (Continued)

(58) Field of Classification Search
  CPC ........ A61B 17/12022; A61B 17/12031; A61B 17/12036; A61B 17/12109; A61B 17/12113; A61B 17/12118; A61B 17/12122; A61B 17/12145; A61B 17/1215; A61B 17/12159; A61B 17/12163; A61B 17/12168; A61B 17/12172; A61B 17/12177; A61B 2017/1205; A61B 2017/12054; A61B 2017/12081; A61B 2017/12095; A61B 17/1204; A61B 17/0057; A61B 2017/00597; A61F 2/013; A61F 2/01–012; A61F 2002/016; A61F 2002/018
  See application file for complete search history.

(56) References Cited

U.S. PATENT DOCUMENTS 5,250,071 A    10/1993  Palermo
5,354,295 A    10/1994  Guglielmi et al.
(Continued)

FOREIGN PATENT DOCUMENTS

AU    768713    6/2001
JP    2002525183    8/2002
(Continued)

*Primary Examiner* — Katherine H Schwiker
(74) *Attorney, Agent, or Firm* — Kacvinsky Daisak Bluni PLLC

(57) ABSTRACT

Expandable occlusive plugs and methods of using them are disclosed. The devices generally include an expandable framework at least partially covered by a membrane. The occlusive plugs can be used for occlusion of body lumens and/or to limit migration of embolic agents to non-target sites.

20 Claims, 2 Drawing Sheets

Figure 1A:
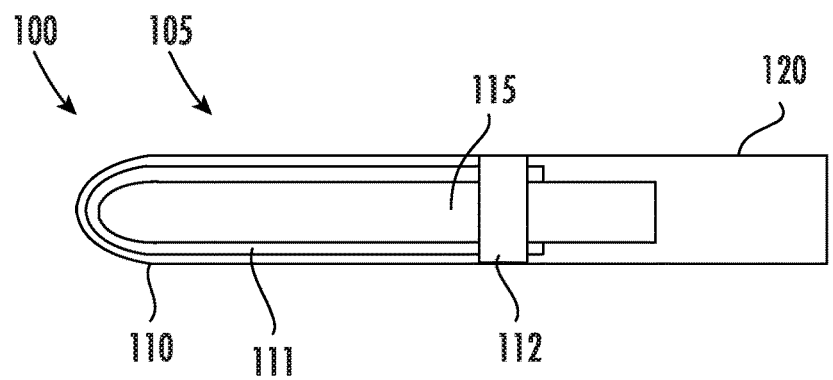

(51) Int. Cl.
*A61B 90/00* (2016.01)
*A61B 17/00* (2006.01)

(52) U.S. Cl.
CPC .. *A61B 17/12113* (2013.01); *A61B 17/12186* (2013.01); *A61B 2017/00867* (2013.01); *A61B 2017/1205* (2013.01); *A61B 2017/12054* (2013.01); *A61B 2017/4216* (2013.01); *A61B 2090/3966* (2016.02)

(56) References Cited

U.S. PATENT DOCUMENTS

| | | | | |
|---|---|---|---|---|
| 5,397,331 | A * | 3/1995 | Himpens | A61B 17/0057 128/899 |
| 6,059,779 | A | 5/2000 | Mills | |
| 6,350,277 | B1 * | 2/2002 | Kocur | A61F 2/90 623/1.11 |
| 8,062,465 | B1 * | 11/2011 | Huang | A61F 2/958 156/308.2 |
| 2003/0093097 | A1 * | 5/2003 | Avellanet | A61B 17/12022 606/157 |
| 2003/0093108 | A1 | 5/2003 | Avellanet et al. | |
| 2004/0044391 | A1 * | 3/2004 | Porter | A61B 17/12022 623/1.1 |
| 2005/0033331 | A1 * | 2/2005 | Burnett | A61F 5/003 606/154 |
| 2006/0293741 | A1 * | 12/2006 | Johnson | A61F 2/86 623/1.11 |
| 2008/0228257 | A1 * | 9/2008 | Richter | A61F 2/95 623/1.11 |
| 2008/0281350 | A1 * | 11/2008 | Sepetka | A61B 17/0057 606/200 |
| 2009/0138036 | A1 * | 5/2009 | Nardone | A61B 17/12022 606/200 |
| 2009/0177261 | A1 | 7/2009 | Teoh et al. | |
| 2013/0131701 | A1 * | 5/2013 | Komlos | A61L 15/38 606/151 |
| 2014/0257361 | A1 * | 9/2014 | Prom | A61B 17/12022 606/198 |
| 2015/0005809 | A1 | 1/2015 | Ayres et al. | |
| 2015/0039019 | A1 * | 2/2015 | Cragg | A61B 17/12172 606/200 |

FOREIGN PATENT DOCUMENTS

| | | |
|---|---|---|
| JP | 2003190175 | 7/2003 |
| JP | 2007517596 | 7/2007 |
| JP | 2014534872 | 12/2014 |
| WO | 2010028300 A1 | 3/2010 |

* cited by examiner

SYSTEMS AND METHODS FOR VASCULAR OCCLUSION

CROSS-REFERENCE TO RELATED APPLICATIONS

This application claims priority under 35 U.S.C. § 119(e) to U.S. Provisional Application Ser. No. 62/138,508, filed on Mar. 26, 2015, herein incorporated by reference in its entirety.

FIELD OF THE INVENTION

This application relates to the field of medical devices. More particularly, the application is related to devices and methods for the occlusion of blood vessels.

BACKGROUND

Embolization involves the partial or complete occlusion of blood vessels, limiting the flow of blood therethrough. The intentional occlusion of blood vessels ("therapeutic embolization") may be used to treat a variety of vascular and non-vascular conditions including cerebral and peripheral aneurysms, arteriovenous malformation and uterine fibroids and to reduce blood flow to solid tumors including liver tumors. Embolization may be achieved by any number of means, including through the use of polymer microspheres, metal coils, metal or polymer plugs, and liquid embolic materials.

In a typical embolization procedure, local anesthesia is first given over a common artery or vein. The artery or vein is then punctured and a catheter is inserted and fluoroscopically guided into the area of interest. An angiogram is performed by injecting contrast agent through the catheter, thereby visualizing the portion of the vascular tree downstream of the distal end of the catheter. Once the catheter is positioned in a site where deposition of an embolic agent is desired, the agent is deposited through the catheter. The embolic agent is generally selected based on the size of the vessel to be occluded, the desired duration of occlusion, and/or the type of disease or condition to be treated, among others factors. Following delivery of the embolic agent to the site within the vessel to be occluded, a follow-up angiogram can be performed to determine the specificity and completeness of the occlusion.

In many common embolic procedures, including sandwich embolization of splanchnic aneurysms, sandwich embolization of gastrointestinal bleeds, embolization of vessels to treat varioceles or pelvic congestion syndrome, and embolization to arrest hemorrhage after trauma, embolization along of a length of blood vessel, rather than at a focal point, is desired. However, embolic coils, which are most commonly used in embolization procedures, are optimally used in focal embolization applications. In practice, users may use multiple embolic coils to pack and fill the length of the vessel, but this approach is time- and material-intensive, as many coils must each be placed individually, increasing the costs of such procedures.

Liquid embolics have recently emerged as a potential alternative to coil-packing procedures. These materials, which include TRUFILL® n-Butyl Cyanoacrylate (n-BCA) (Codman & Shurtleff, Inc., Raynham, Mass.) and ONYX® ethylene vinyl alcohol copolymer (EVOH) (ev3 Endovascular, Inc., Plymouth, Minn.), can be expensive (up to $2,500 per mL in the case of EVOH embolics) and, when deployed in vessels with relatively high flow rates, may be prone to migration and embolization of non-target areas. To prevent such migration, practitioners may deploy coils on either side (i.e. the proximal and/or distal sides) of a polymerized liquid embolic mass, further reducing blood flow and reducing the risk of such nontarget embolizations. This approach, however, also requires multiple steps, and may require the use of multiple catheters, particular as most liquid embolics (such as n-BCA) solidify within the catheter, necessitating the placement of a new catheter if deployment of an embolic coil proximal to the polymerized liquid embolic mass is desired.

Another alternative to packing vessels with conventional embolic coils and/or liquid embolics is to use multiple hydrogel-coated embolic coils, such as the AZUR™ coil (Terumo Medical Corporation, Somerset, New Jersey); these coils expand in volume when exposed to aqueous environments, allowing them to occupy more space than conventional embolic coils having an equivalent pre-deployment diameter. Even so, procedures involving these devices will typically require placement of multiple coils, and will thus involve greater complexity and expense than interventions which require only a single deployment step.

Additionally, in many embolization procedures, particularly occlusion of an ostium or branch of a blood vessel, deployment of embolic materials with high specificity is desired. But the specificity of occlusion can be reduced by the tendency of the occlusive device or material to become displaced during deployment (termed "kickback" or "jumping" in the case of embolic coils and plugs). In the vascular occlusion setting, such kickback can result in incomplete embolization or even non-target embolization. In general, occlusive plug devices tend to be less prone to kickback than embolic coils, and may be preferred in applications where kickback is particularly undesirable, but in selecting plugs vs. coils, users are presented with another tradeoff: occlusive plus such as the Amplatzer™ occlusive plugs (St. Jude Medical, Minneapolis, Minn.) generally have a larger profile than embolic coils, and are not well suited to be deployed through or into narrow or tortuous vessels.

SUMMARY OF THE INVENTION

The present invention, in its various aspects, addresses the shortcomings of existing coil and liquid embolics, and provides systems and methods for single-step delivery of embolics across a vascular length, rather than at a focal point.

In one aspect, the present invention relates to a system for treating a patient that includes an expandable occlusive plug which in turn has an elongate shaft and, disposed at a distal end of the shaft, a flexible framework at least partially covered by a membrane, which flexible framework can move between a first (compressed) configuration characterized by a first diameter and a second (expanded) configuration characterized by a relatively larger second diameter. The system has a number of optional features, including in some cases a framework that includes a pair of crossed wires and/or a shape memory material. The flexible framework can include first a first end secured to the elongate shaft, and a second end opposite the first end; in some cases, the first end of the framework is located is the distal end of the device, while in other cases the second end is at the distal end. In some cases, the flexible framework and the membrane define a cone or umbrella shape when expanded into the second configuration. The system can also include a catheter and a pushrod, in which case the expandable occlusive plug is slidable within the catheter when in the first configuration and the expandable occlusive plug optionally assumes the second configuration when it is not inside the catheter. The membrane, which can be (but is not necessarily) disc shaped or round is, in some cases, is a synthetic polymer such as poly(ethylene terephthalate), polyvinylidene fluoride, polytetrafluoroethylene (PTFE), expanded PTFE, polyurethane or silicone. The flexible framework can include two or more elongate elements fused together in an X shape, or alternatively, it can include two or more wires connected at a first end and connected or constrained (e.g. by a bushing, eyelet, etc.) such that the framework has a taper, in the second configuration, from a minimal diameter at the first end to a maximal diameter between the first and second ends and to a third diameter less than the second diameter at the second end. Systems according to this aspect of the invention can be used in medicine, for instance in the occlusion of a blood vessel.

In another aspect, the present invention relates to an expandable embolic plug that includes an elongate shaft, a flexible framework disposed at a first end of the elongate shaft, which framework is at least partially covered by a polymer membrane. As discussed above, the framework moves between a first configuration characterized by a first diameter and a second configuration characterized by a second diameter larger than the first diameter. The plug has several optional features. First, the flexible framework may include a pair of crossed nitinol wires, or the framework may have a first end secured to the elongate shaft and a second end opposite the first end; in these latter cases, the first end may be disposed at a distal end of the plug, or the second end may be disposed at the plug's distal end. In some cases, the plug includes a polymer sleeve disposed about the plug at or near the second end of the framework, which sleeve is sized to hold the flexible framework in the first configuration and configured to dissolve, degrade or erode when placed in a blood vessel of a patient.

In yet another aspect, the present invention relates to a method of treating a patient by inserting an expandable occlusive plug into a blood vessel of a patient. The plug, which includes an elongate shaft and a polymer-membrane covered flexible framework disposed at a first end of the elongate shaft, is moveable between first (compressed) and second (expanded) configuration. The plug is insertable into the blood vessel by means of a catheter or microcatheter (e.g. inserting the distal end of the microcatheter into the blood vessel and then discharging the plug into the blood vessel. In some cases, a liquid embolic material is then flowed through the catheter so that it contacts the plug within the blood vessel.

DRAWINGS

Aspects of the invention are described below with reference to the following drawings in which like numerals reference like elements, and wherein:

FIG. 1A through 1D shows schematic views of snare occlusion devices according to certain embodiments of the present invention in various stages of deployment.

Figure 2A:
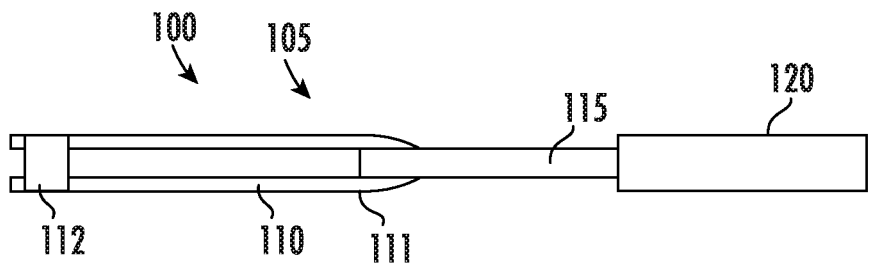
Figure 2B:
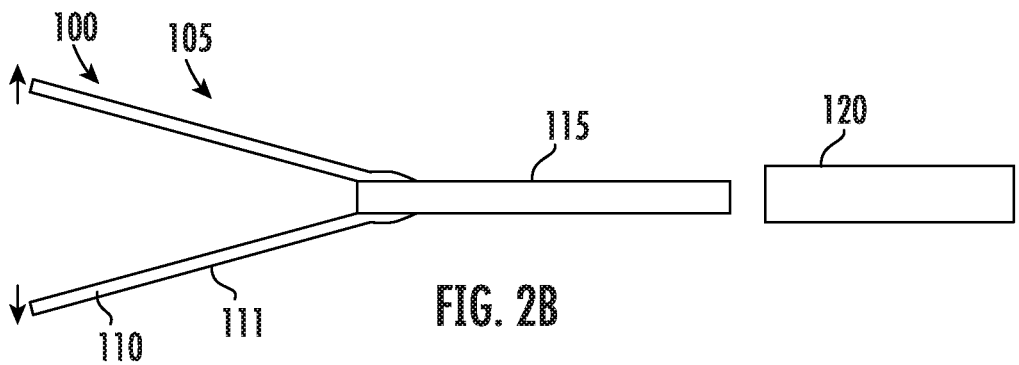
Figure 2C:
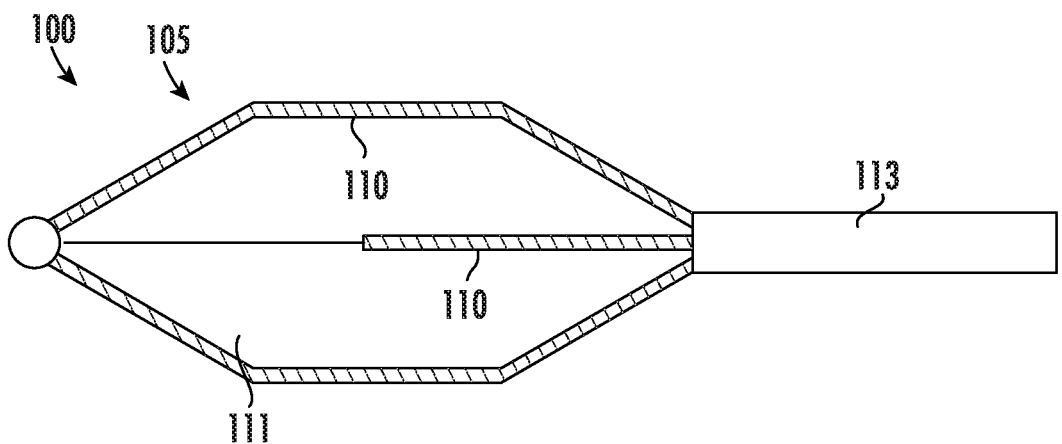

FIG. 2A through C shows schematic views of snare occlusion devices according to alternate embodiments of the present invention.

Unless otherwise provided in the following specification, the drawings are not necessarily to scale, with emphasis being placed on illustration of the principles of the invention.

DETAILED DESCRIPTION OF THE PREFERRED EMBODIMENTS

Turning to FIG. 1, an exemplary occlusion device 100 according to one group of embodiments of the present invention comprises an expandable occlusive element 105 having at least two components: an expandable framework 110 and a membrane 111 secured to at least a portion of the framework 110. The occlusive element 105 also preferably includes a central shaft 115 that is reversibly coupled to a pushrod 120 to facilitate delivery of the device 100 through a catheter and into a body lumen such as a blood vessel. The occlusive element 105 is preferably moveable between compressed (small diameter) and expanded (large diameter) configurations, to facilitate delivery of the occlusive device 100 through a relatively narrow gauge catheter into a larger-diameter blood vessel, where the occlusive element 105 generally expands to contact the inner wall of the vessel and to apply sufficient radially-outward force to the vessel to limit or prevent migration of the occlusive device 100 after it is deployed.

The framework 110 is preferably made from two or more pieces of 0.03" (0.762 mm) to 0.06" (1.524 mm) nitinol wire brazed, soldered, or otherwise attached to form a symmetrical "X" or other radially symmetrical shape, which is then heat-treated to bias the framework 110 into an open configuration. While nitinol is the preferred material for the framework 110, though other materials such as stainless steel, shape-memory polymers, platinum, or poly-lactic acid (PLA) and/or poly-lactic-co-glycolic acid (PLGA) are used in some instances. Thereafter, a sheet 111 (preferably, but not necessarily disc-shaped i.e. round) of polymer film (such as poly(ethylene terephthalate) (PET), polyvinylidene fluoride (PVDF), polytetrafluoroethylene (PTFE) or expanded PTFE (ePTFE), polyurethane or silicone) is adhered to the framework 110. To place the device 100 into the compressed configuration, the nitinol posts of the framework 110 are bent radially inward toward the center and constrained there, for instance by a removable or dissolvable sleeve 112, which is preferably formed from a water soluble polymer, such as polyvinylpyrrolidone (PVP), polyvinyl alcohol (PVA) and/or polyethylene glycol (PEG). When compressed, the device 100 has an outer diameter selected to permit delivery through a microcatheter, such as 0.021" (0.533 mm/4 Fr), 0.025" (0.635 mm/5 Fr) 0.027" (0.686 mm) and so on, up to sizes that approximate currently-used devices, such as 0.066" (1.667 mm/5 Fr) but which are useful to occlude significantly larger blood vessels. In general, the outer diameter of the device 100 in the compressed configuration is slightly less than the inner diameter of the microcatheter being used (e.g. 0.025" for use in a 0.027" catheter)

The central shaft 115 couples to a pushrod 120, optionally by means of a severable link or joint, a threaded screw. Exemplary detachment mechanisms for medical implants are described in, inter alia U.S. Pat. Nos. 5,250,071 (describing interlocking clasp mechanisms incorporating complementary male and female ends), 5,354,295 (describing electrolytically severable core wires), 6,059,779 (describing annular return electrodes disposable about electrolytically severable core wires), and US pre-grant publication no. 20090177261 (describing detachment mechanisms utilizing materials that change shape in response to the application of heat or electrical energy, including synthetic polymers). Each of the foregoing references is hereby incorporated by reference in its entirety and for all purposes. Alternatively, the central shaft 115 is coupled to the pushrod 120 by means of a water soluble sleeve such as sleeve 112

In some cases, the membrane 111, the central shaft 115, or any other portion of the device 100 includes a coating, which is, variously, adhesive to improve adhesion of the device 100 to the inner wall of the vessel in which it is deployed, or hydrophilic (e.g. bioslide™ hydrophilic coating, Boston Scientific, Marlborough, Mass.), or hydrophobic (e.g. polytetrafluoroethylene (PTFE), silicone) to facilitate adhesion of a hydrophobic embolic material 120 such as a foam to the device. Portions of the device 100 can also include an iodinated coating and/or a discrete fluoroscopic marker such as a platinum, palladium or tungsten band or other marker. Additionally, a mucosal adhesive of the modified acrylate type is also employed in some cases for improved adhesion of the snare device to the artery/vessel wall.

Figure 1B:
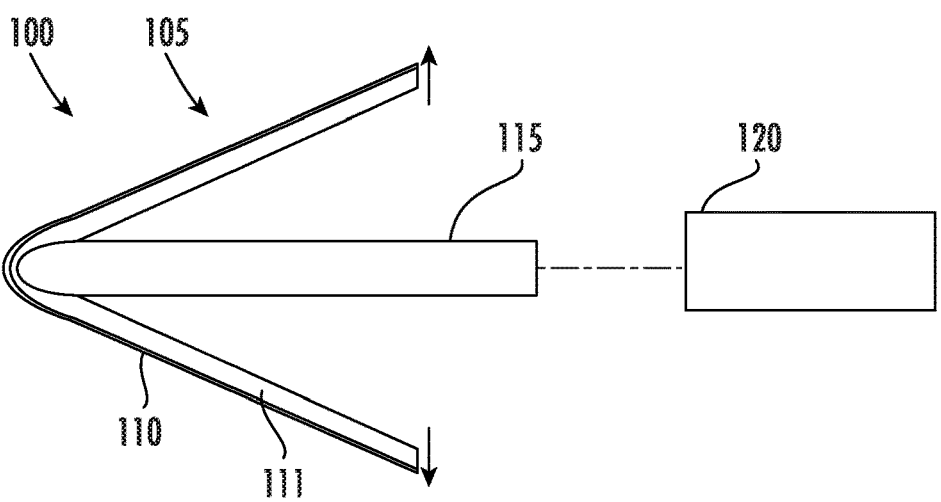
Figures 1C, 1D:
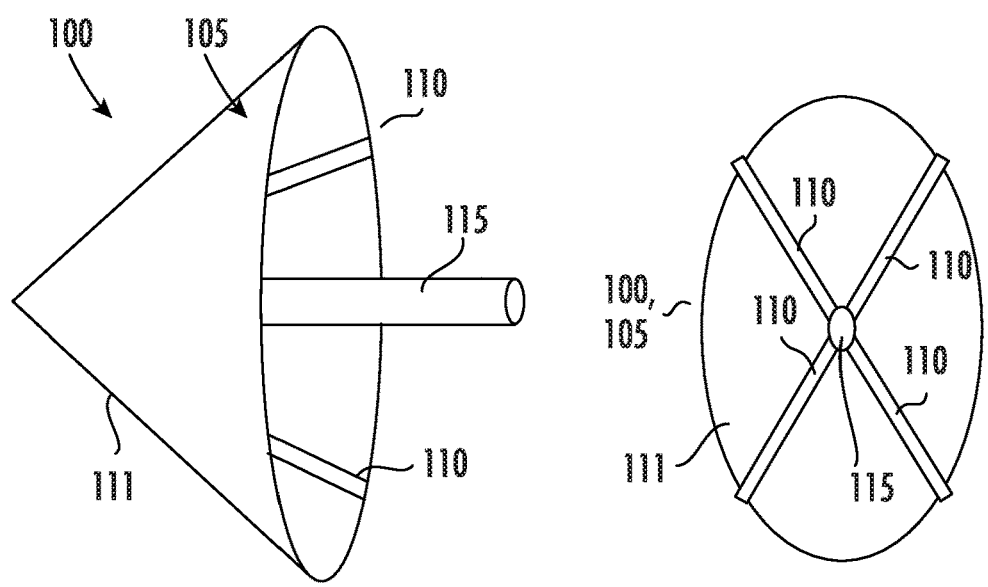

In use, the occlusion device 100 is inserted into a blood vessel by means of a microcatheter, (not shown), according to a process generally illustrated in FIGS. 1A-B. The process begins with the insertion of the catheter into the patient's vasculature, such that a distal end of the catheter is proximate to, or within, a length of blood vessel where occlusion is desired. When the catheter is so positioned, the pushrod 120 is advanced so that the device 100 extends distally through a distal aperture of the catheter and into the vessel (alternatively, the catheter is retracted over the device 100 and the pushrod 120, thereby allowing the device 100 to expand in place during this step). During or after the placement of the device 100 into the vessel, the sleeve 112 constraining the diameter of the occlusive element 105 preferably dissolves, disintegrates etc. by reaction with an aqueous material (e.g. water) in the blood vessel, allowing the framework 110 and membrane 111 to expand radially outward to contact an interior wall of the blood vessel, as shown in FIGS. 1B-D. When deployed, the device 100 has a generally umbrella-shaped profile, as shown in FIGS. 1C-D.

Following expansion of the occlusive element 105, the device is optionally pushed to a position distal of its desired final position, and then pulled back. Thereafter, a liquid embolic is optionally (but not necessarily) flowed through the catheter into the space defined by the distal end of the catheter and the occlusive element 105. The liquid embolic can be any material that polymerizes, cross-links, viscifies, or otherwise changes from a liquid to a gel or solid in situ (which processes are referred to throughout this application, for ease of presentation, as "hardening") following deployment into a blood vessel, such as n-BCA or EVOH. After the liquid embolic has hardened, the link between the pushrod 120 and the central shaft 115 is severed, such that the occlusive element 105 and central shaft 115 remain in place and attached to the embolic material forming an indwelling implant. Severing of the link between pushrod 120 and central shaft 115 is facilitated, in preferred embodiments, by the use of a severable link or joint, which can be a mechanically, electrolytically or thermally severable structure.

Alternate embodiments of the present invention are shown in FIGS. 2A-C. In a first alternate embodiment, shown in FIGS. 2A-B, the occlusive element 105 is repositioned to open opposite the central shaft 115, rather than toward the central shaft 115 as in the embodiments described above; this arrangement advantageously reduces the risk of lateral translation or "jumping" of the device 100 during deployment, and facilitates resheathing of the device simply by advancing the catheter over the device 100, thereby compressing the occlusive element 105 and allowing the device 100 to be repositioned by a user (though such repositioning preferably occurs prior to the severing of any link between the pushrod 120 and the central shaft 115). In other embodiments, the framework 110 comprises a plurality of shape-memory wires which are connected at a distal end of the occlusive element 105 and which are constrained within an overtube 113 prior to deployment, and which are advanced distally through the overtube 113 during deployment; once extended through the catheter, they expand to form a structure similar to the umbrella-like structures described above.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An occlusive system, comprising:
   an expandable device comprising:
   an elongate shaft comprising a distal end and a proximal end;
   a flexible framework comprising a distal end disposed at the distal end of the elongate shaft, a proximal end, and a length therebetween, the flexible framework moveable between a compressed configuration wherein the proximal end of the flexible framework has a first outer diameter and an uncompressed configuration wherein the proximal end of the flexible framework has a second outer diameter larger than the first outer diameter; and a membrane at least partially covering the flexible framework;

a pushrod comprising a distal tip configured to deliver the expandable device; and a dissolvable sleeve disposed along the flexible framework proximate the proximal end of the framework and having a length flexible less than the length of the flexible framework, the dissolvable sleeve further disposed about the distal tip of the pushrod, the dissolvable sleeve configured to constrain the proximal end of the flexible framework in the compressed configuration, and the dissolvable sleeve configured to detachably couple the proximal end of the elongate shaft to the distal tip of the pushrod.

2. The system of claim 1, wherein the flexible framework is bent radially inward against the elongate shaft in the compressed configuration.

3. The system of claim 1, wherein the flexible framework is constrained about a surface of the elongate shaft in the compressed configuration.

4. The system of claim 1, wherein the distal end of the flexible framework is distal to the dissolvable sleeve in the compressed configuration.

5. The system of claim 1, wherein the first outer diameter is less than an inner diameter of a lumen of a delivery catheter configured to receive the occlusive system with the flexible framework in the compressed configuration.

6. The system of claim 1, wherein the dissolvable sleeve comprises a dissolvable polymer.

7. The system of claim 1, wherein the flexible framework comprises a pair of crossed wires with midportions of the wires disposed at the distal end of the elongate shaft.

8. The system of claim 1, wherein the flexible framework comprises a shape memory material.

9. The system of claim 1, wherein the flexible framework and membrane define a cone or umbrella shape when in the uncompressed configuration.

10. An occlusive system, comprising:
an expandable device comprising:
an elongate shaft comprising a proximal end and a distal end;
a flexible framework comprising a plurality of wires with wire ends, each wire having a midportion disposed at the distal end of the elongate shaft and the wire ends of each wire bendable towards the proximal end of the elongate shaft, the flexible framework moveable between a compressed configuration wherein the wire ends of the plurality of wires form a first outer diameter and an uncompressed configuration wherein the wire ends of the plurality of wires form a second outer diameter larger than the first outer diameter; and a membrane covering at least a portion of the flexible framework;

a pushrod comprising a distal tip configured to deliver the expandable device; and a dissolvable sleeve disposed about the wire ends of the plurality of wires and proximal to the midportion of the plurality of wires, the dissolvable sleeve further disposed about the distal tip of the pushrod, the dissolvable sleeve configured to constrain the flexible framework in the compressed configuration and detachably couple the proximal end of the elongate shaft to the distal tip of the pushrod.

11. The system of claim 10, wherein the flexible framework is constrained about a portion the elongate shaft in the compressed configuration.

12. The system of claim 10, wherein the plurality of wires cross each other at the midportion of each wire.

13. The system of claim 10, wherein the first outer diameter is less than an inner diameter of a lumen of a delivery catheter configured to receive the occlusive system with the flexible framework in the compressed configuration.

14. The system of claim 10, wherein the dissolvable sleeve comprises a dissolvable polymer.

15. The system of claim 10, wherein the plurality of wires comprises a pair of crossed wires.

16. The system of claim 10, wherein the flexible framework and membrane define a cone or umbrella shape when in the uncompressed configuration.

17. A method of delivering an occlusive device, comprising:
inserting an occlusive device into a body lumen via a distal end of a pushrod, the device comprising a flexible framework constrained by a dissolvable sleeve about an elongate member, the dissolvable sleeve having a length less than the length of the flexible framework, the dissolvable sleeve configured to detachably couple a proximal end of the elongate shaft to a distal tip of the pushrod;
delivering the occlusive device into the body lumen by exposing the occlusive device to a body fluid such that the dissolvable sleeve dissolves, allowing the flexible framework to transition from a compressed configuration to an uncompressed configuration and the elongate member to detach from the distal tip of the pushrod.

18. The method of claim 17, wherein the flexible framework transitions from the compressed configuration to the uncompressed configuration and the elongate member detaches from the distal end of the pushrod, simultaneously.

19. The method of claim 17, wherein the dissolvable sleeve is distal a proximal end of the flexible framework.

20. The method of claim 17, wherein the flexible framework comprises a pair of crossed wires with midportions of the wires disposed at a distal end of the elongate member.

* * * * *